US00PP31880P3

(12) United States Plant Patent
Suphachadiwong

(10) Patent No.: US PP31,880 P3
(45) Date of Patent: Jun. 16, 2020

(54) ***VANDA* PLANT NAMED 'SPCDW1801'**

(50) Latin Name: ***Vanda* spp. Jones ex R. Br.**
Varietal Denomination: SPCDW1801

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 16/501,450

(22) Filed: Apr. 17, 2019

(65) Prior Publication Data

US 2019/0320570 P1 Oct. 17, 2019

(30) Foreign Application Priority Data

Apr. 17, 2018 (QZ) ..... PBR 2018/1051

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

*Primary Examiner* — Susan McCormick Ewoldt
(74) *Attorney, Agent, or Firm* — Samuel R. McCoy, Jr.

(57) ABSTRACT

A new and distinct *Vanda* plant named 'SPCDW1801' which is characterized by a symmetrical distichous foliage arrangement with flowers held above the foliage, a light purple dorsal sepal and light purple lateral petals which are dotted with dark purple, dark purple lateral sepals that are margined light purple-violet, a labellum with a dark purple to greyed-purple central lobe and dark purple lateral lobes which are radially striped green-white, and the stability of these characteristics from generation to generation.

4 Drawing Sheets

CROSS REFERENCE TO RELATED APPLICATIONS

This application claims priority to the Community Plant Variety Rights application number 2018/1051, filed Apr. 17, 2018, which is herein incorporated by reference.

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1801'.

BACKGROUND OF THE INVENTION

Parentage: The new *Vanda* plant, 'SPCDW1801', is the result of a planned breeding program. 'SPCDW1801' originated as a seedling from the controlled pollination of *Vanda* 'D25M' (not patented), the seed parent, with *Vanda* '370MK' (not patented), the pollen parent. Both parents were developed by, and are owned by, the inventor and were never commercially released. The crossing was made by the inventor in his research greenhouse in Bangphra, Thailand in June of 1993.

The new variety was first selected in January of 1998, in a research greenhouse in Bangphra, Thailand belonging to the inventor. After identifying the new variety as a potentially interesting selection, the inventor continued confidential testing and propagation of 'SPCDW1801', assessing stability of the unique characteristics of this variety.

Asexual Reproduction: Asexual reproduction of the new cultivar 'SPCDW1801', by way of mericloning, was first initiated in April of 2011 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1801' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1801'. These characteristics in combination distinguish 'SPCDW1801' as a new and distinct *Vanda* cultivar:

1. *Vanda* 'SPCDW1801' exhibits a symmetrical distichous foliage arrangement with flowers held above the foliage; and
2. *Vanda* 'SPCDW1801' exhibits a light purple dorsal sepal and light purple lateral petals which are margined with purple-violet, and dotted with dark purple; and
3. *Vanda* 'SPCDW1801' exhibits dark purple lateral sepals which are margined purple-violet; and
4. *Vanda* 'SPCDW1801' exhibits a labellum with a dark purple to greyed-purple central lobe, and dark purple lateral lobes which are radially striped green-white.

BOTANICAL DESCRIPTION OF THE PLANT

Figure 1:
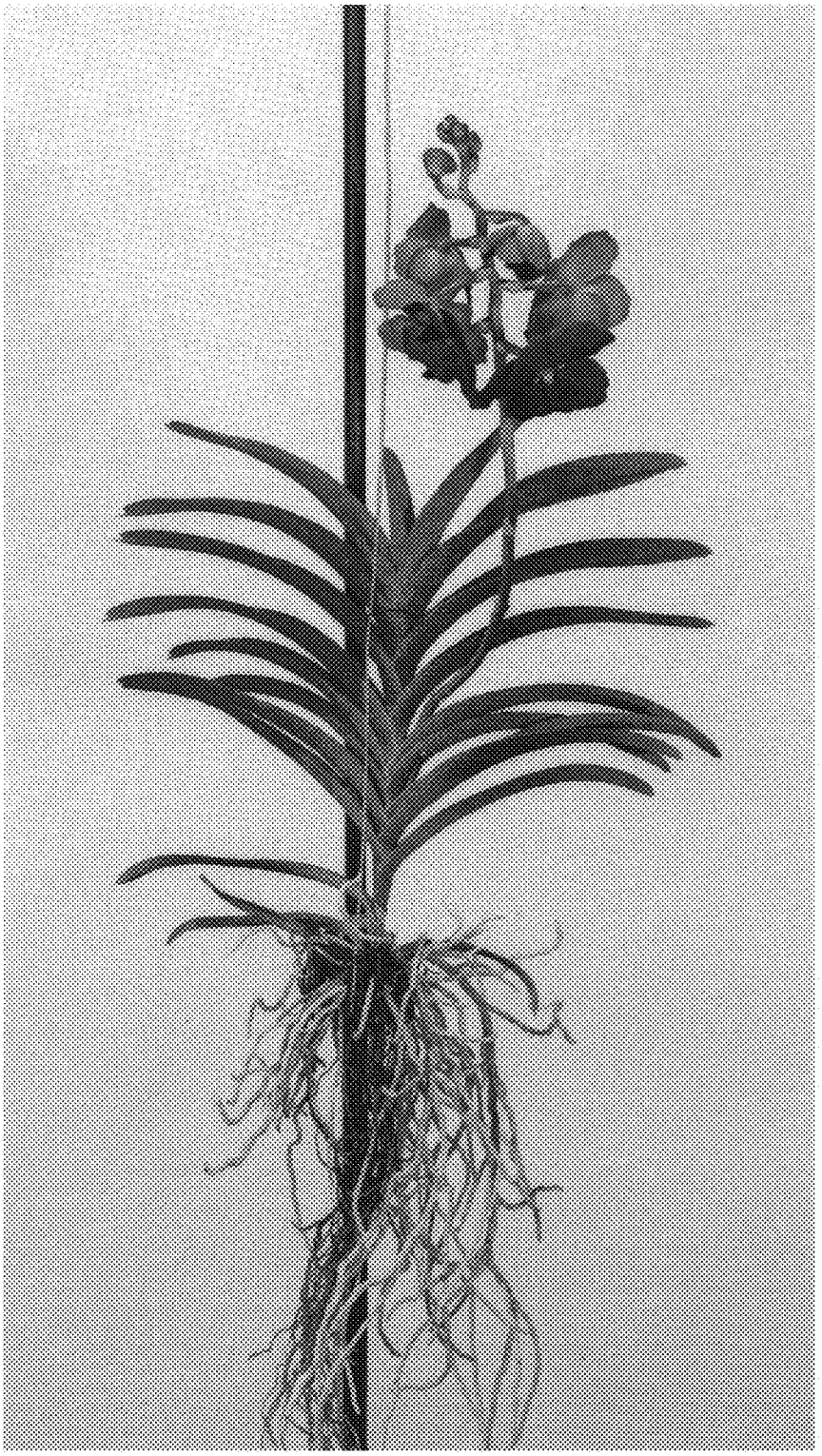
FIG. 1 illustrates, as nearly true as it is reasonably possible to make the same in color photographs of this type, an exemplary plant of 'SPCDW1801' grown in a commercial greenhouse in Honselersdijk, the Netherlands. This plant is approximately 6 years old from the time of mericloning, shown planted in an 8 by 2 cm container.
Figure 2:
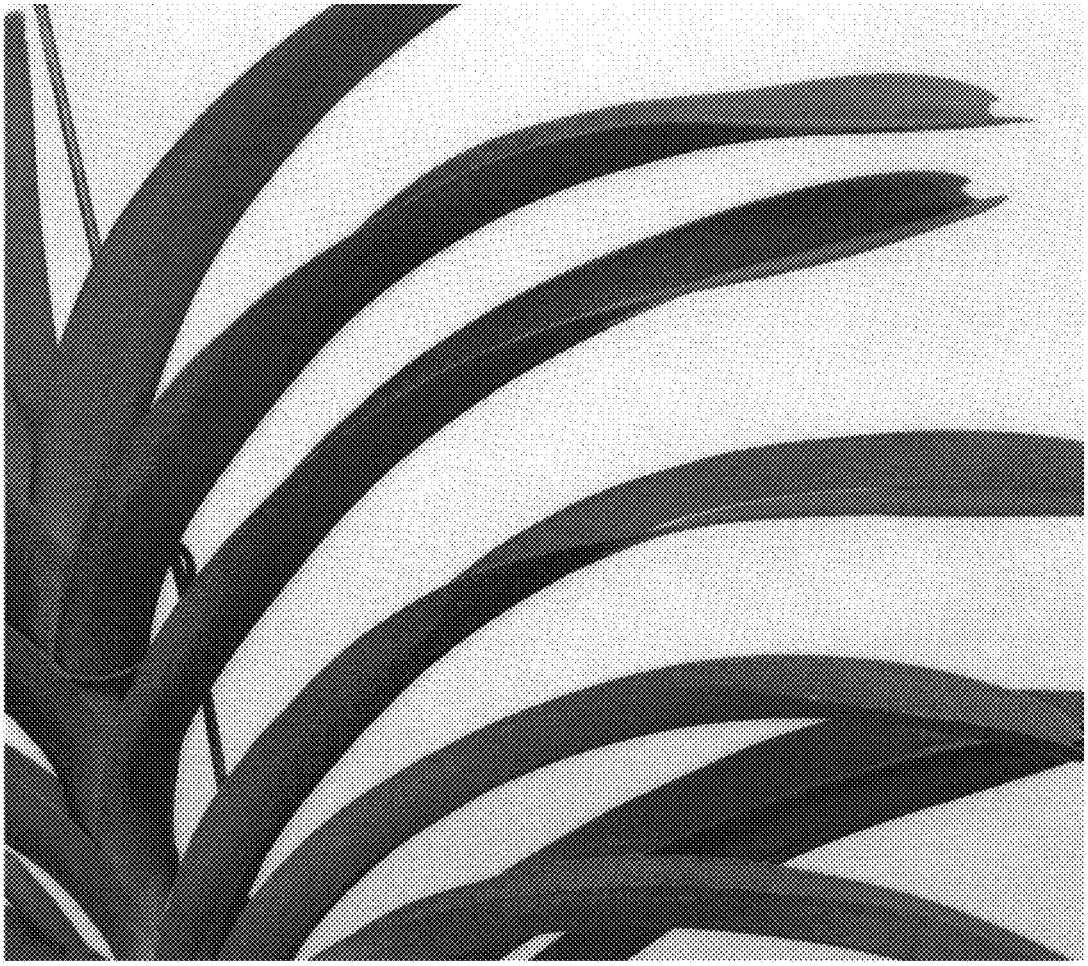
FIG. 2 illustrates, as nearly true as it is reasonably possible to make the same in color photographs of this type, the typical foliage of 'SPCDW1801'.
Figure 3:
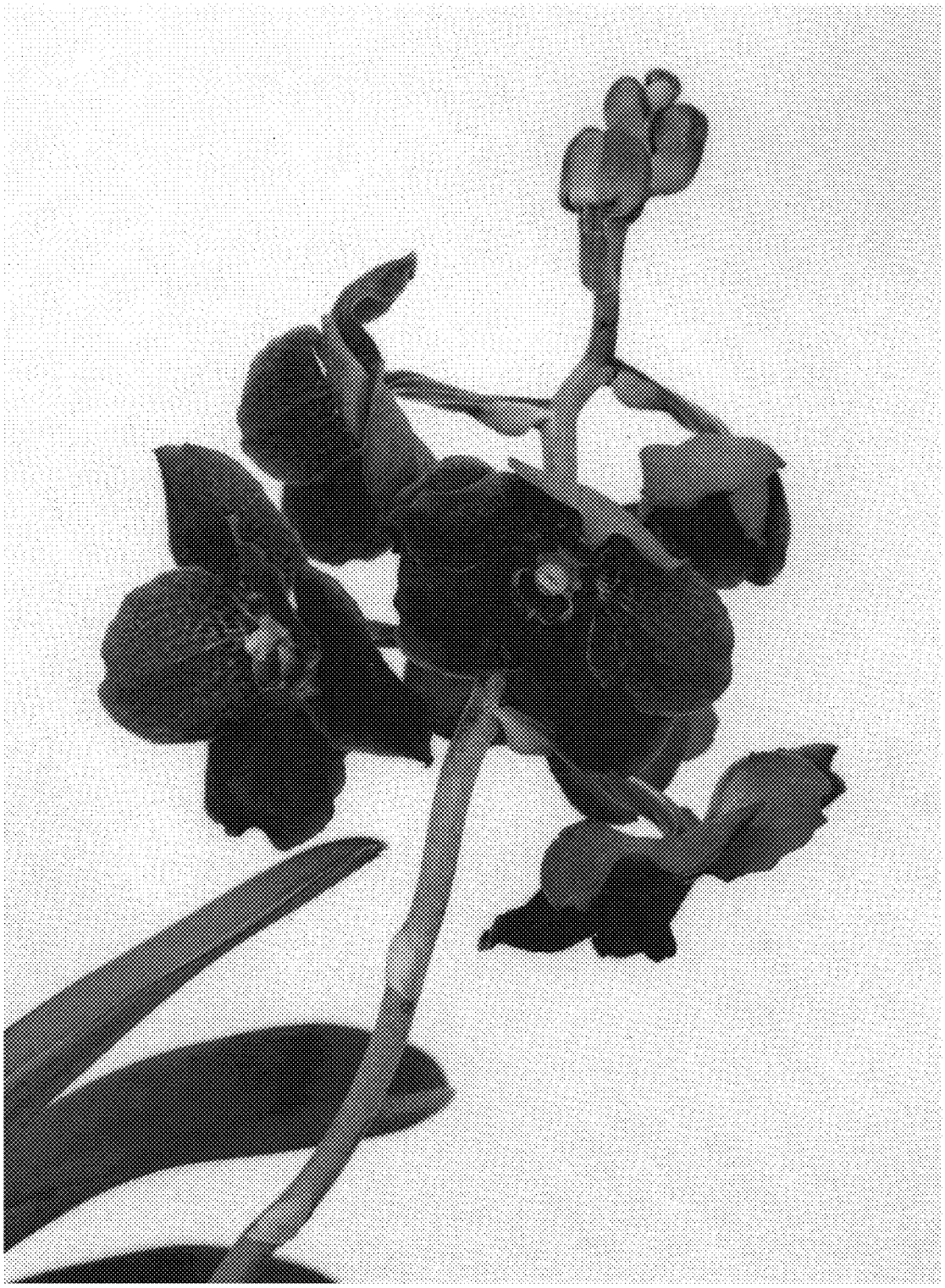
FIG. 3 illustrates, as nearly true as it is reasonably possible to make the same in color photographs of this type, the typical inflorescence of 'SPCDW1801'.
Figure 4:
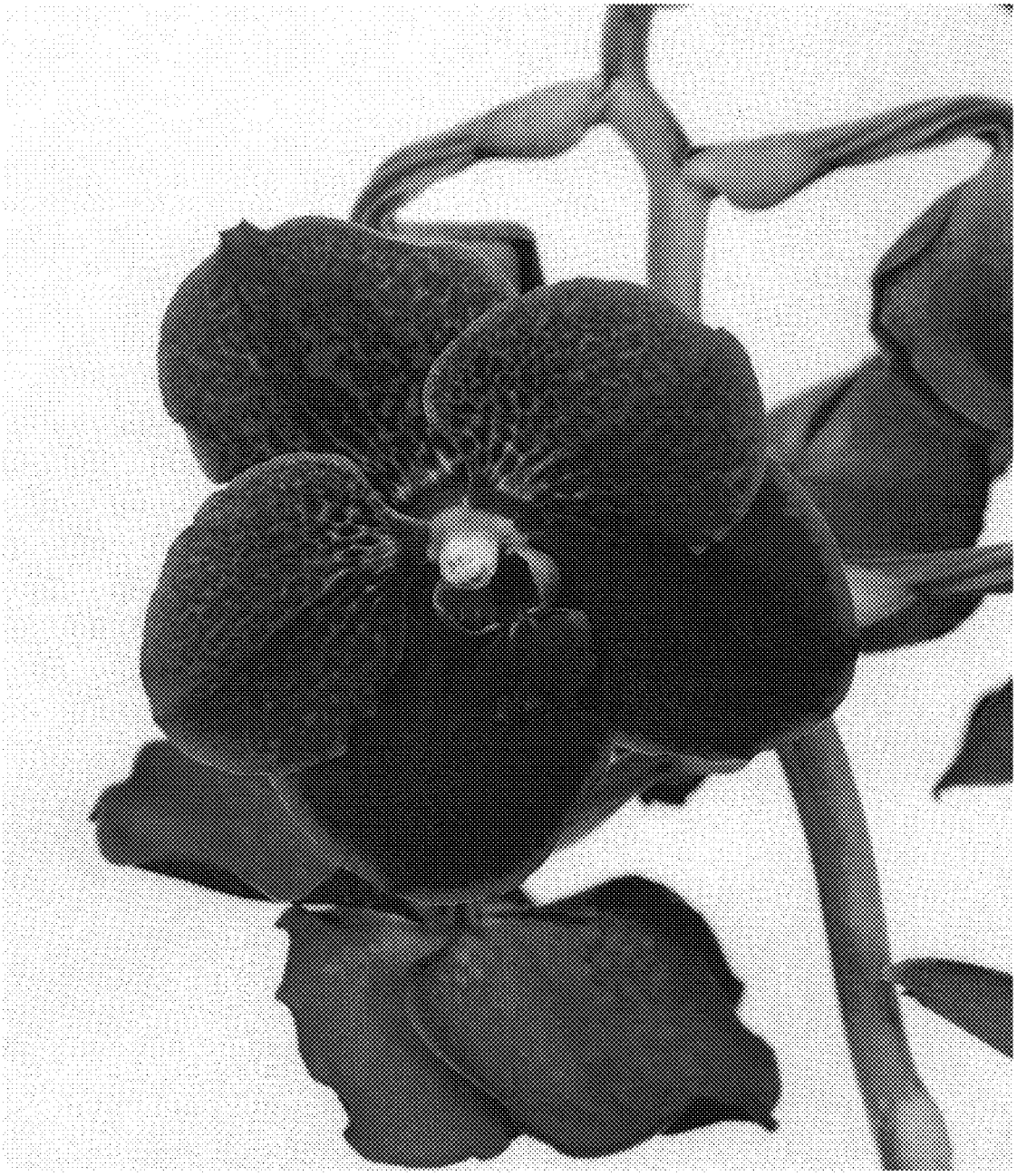
FIG. 4 illustrates, as nearly true as it is reasonably possible to make the same in color photographs of this type, the typical flower of 'SPCDW1801'.

The following observations and measurements made in March of 2019 describe averages from a sample set of six specimens of six year-old 'SPCDW1801' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1801' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'SPCDW1801' and comparisons with the parents and most similar commercial variety of *Vanda* are provided below.

Plant description:

- *Growth habit.*—Perennial; monopodial, upright. Single monopodial leafy stem, with flowers carried above the leaf plane; inflorescences growing from the leaf axils.
- *Average height from base (plant grown in hanging basket, so no soil line present) to foliar plane.*—40.8 cm.
- *Average height from base (plant grown in hanging basket, so no soil line present) to top of floral plane.*—59.0 cm.
- *Plant spread.*—Average of 38.6 cm.
- *Appropriate container size.*—8 cm by 2 cm rectangular hanging basket.
- *Growth rate.*—Moderate.
- *Plant vigor.*—Moderate.
- *Propagation type.*—Meristematic tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Plants have not been observed to be susceptible or resistant to pathogens and pests common to *Vanda*.
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Moderately to densely rooting; with aerial roots only.
- *Dimensions, mature roots.*—42.4 cm long with a diameter of 0.5 cm, on average.
- *Texture.*—Very fleshy; non-fibrous.
- *Color.*—Greyed-green, nearest to RHS 192C; root apex is yellow-green, RHS 148A.

Stem:

- *Branching habit.*—Monopodial; no lateral branches present.
- *Number of primary (main) stems per plant.*—One.
- *Number of secondary (lateral) branches per plant.*—None.
- *Aspect.*—Circular, formed by the leaf sheaths.
- *Length.*—26.0 cm.
- *Diameter.*—0.9 cm.
- *Internode length.*—1.2 cm.
- *Pubescence.*—Glabrous.
- *Luster.*—Matte.
- *Attitude, main stem.*—Near vertical.
- *Strength.*—Very strong.
- *Color, juvenile.*—Yellow-green, nearest to RHS 145D.
- *Color, mature.*—Yellow-green, nearest to RHS 145C.
- *Color at internodes.*—Yellow-green, nearest to RHS 145C.

Foliage:

- *Arrangement.*—Distichous.
- *Dimensions.*—25.5 cm long, excluding the sheath, and 2.9 cm wide.
- *Shape of blade.*—Ligulate.
- *Aspect.*—Moderately to strongly carinate and very slightly curled inward.
- *Attitude.*—Slightly to moderately curled downward.
- *Apex.*—Unequal praemorse.
- *Base.*—Sheathing.
- *Sheath dimensions.*—2.5 cm long and 1.1 cm wide, on average.
- *Sheath color.*—Yellow-green, nearest to a mixture of RHS 144B and 144C.
- *Margin.*—Entire.
- *Pubescence, texture and luster of adaxial surface.*—Glabrous, smooth, and matte.
- *Pubescence, texture and luster of abaxial surface.*—Glabrous, smooth, and matte.
- *Color.*—Juvenile foliage, adaxial surface — Yellow-green, nearest to RHS 144A, and becoming green towards the margins and apex, nearest to RHS 137A. Juvenile foliage, abaxial surface — Yellow-green, nearest to RHS 144A. Mature foliage, adaxial surface — Green, nearest to RHS NN137B. Mature foliage, abaxial surface — Yellow-green, nearest to RHS 146A.
- *Venation.*—Pattern — Parallel. Color, adaxial surface — Green, nearest to RHS NN137B. Color, abaxial surface — Green, nearest to RHS 143B.
- *Petiole.*—No petioles present; leaves sessile.

Inflorescence:

*Inflorescence arrangement.*—Axially placed raceme.

*Natural flowering season.*—Autumn into winter.

*Time to flower.*—Approximately 10 months.

*Flowers per inflorescence.*—Average of 11.

*Flowers per plant.*—6 open flowers and 5 flower buds.

*Inflorescence height.*—Approximately 21.2 cm (measured from base of lowest flower to top of upper flower).

*Inflorescence diameter.*—Approximately 17.9 cm.

*Peduncle.*—Dimensions — Approximately 46.8 cm long and 0.75 cm wide. Attitude — Generally at a 20 degree angle to lateral branch axis. Strength — Moderately strong. Texture and luster — Glabrous and slightly glossy. Color — Nearest to in between green and yellow-green, RHS 143B and 144A.

Bud:

*Length.*—Average of 1.9 cm.

*Diameter.*—Average horizontal diameter is 1.9 cm; the vertical diameter is 2.1 cm.

*Shape.*—Cubic, with a deltoid apex which is pointed downward.

*Pubescence, texture and luster.*—Glabrous, smooth and slightly glossy.

*Color.*—Purple, nearest to RHS N79B, and suffused with a darker shade of purple towards the apex, nearest to RHS N79A; base is yellow-green, nearest to RHS 142C.

Flower:

*Flower type.*—Zygomorphic (orchidaceous), typical shape for the genus *Vanda*.

*Flowering habit.*—Moderately free flowering.

*Shape.*—Zygomorphic, single; consisting of three sepals and three petals, one of which is transformed into a labellum; the two lateral petals strongly overlap the lateral sepals and moderately overlap the dorsal sepal; lateral sepals moderately overlap one another.

*Attitude.*—Flowers are outward-facing to moderately nodding.

*Vertical height.*—Approximately 9.8 cm.

*Diameter.*—Approximately 9.4 cm.

*Depth.*—Approximately 3.6 cm.

*Fragrance.*—No fragrance.

*Lastingness.*—3 weeks, on average.

*Persistent.*—Self-cleaning.

*Petals.*—Quantity of Petals — Three unfused petals; two conventional petals and one labellum. Arrangement — One lateral petal on each side. Length — Approximately 4.4 cm. Width — Approximately 4.0 cm. Shape — Broad ovate. Apex — Obtuse. Base — Cuneate. Margin — Entire; slightly undulated. Pubescence, texture and luster of upper surface — Glabrous, velvety and matte. Pubescence, texture and luster of lower surface — Glabrous, velvety and matte. Color when opening, upper surface — Purple, nearest to in between RHS NN78A and N79C; fading lighter towards the base, nearest to RHS 76C; becoming purple-violet towards the apex, nearest to RHS N81A; base of petals is purple, nearest to RHS 76B; petals are dotted with purple, nearest to RHS N79A. Color when opening, lower surface — Purple-violet, nearest to RHS N82A, and fading to green-white towards the base, nearest to RHS 157A. Color when fully opened, upper surface — Purple, nearest to in between RHS N78A and N79C; fading lighter towards the base, nearest to a mixture of RHS 76C and 76D; becoming purple-violet towards the apex, nearest to RHS N81B; base of petals is purple, nearest to RHS 76B; petals are dotted with purple, nearest to in between RHS N77A and N79A. Color when fully opened, lower surface — Purple-violet, nearest to RHS N82A, and fading to green-white towards the base, nearest to RHS 157A. Fading, upper surface — Not fading. Fading, lower surface — Not fading. Venation color, fully opened, upper surface — Purple, nearest to in between RHS N78A and N79D; fading lighter towards the base, nearest to a mixture of RHS 76C and 76D; becoming purple-violet towards the apex, nearest to RHS N81B; base of petals is purple, nearest to RHS 76B; petals are dotted with purple, nearest to in between RHS N77A and N79A. Venation color, fully opened, lower surface — Purple-violet, nearest to RHS N82A, and fading to green-white towards the base, nearest to RHS 157A.

*Labellum.*—Shape — Three-lobed; the lateral lobes are obovate and involute; the central lobe is broad oblong and revolute. Length — Central lobe — Approximately 2.0 cm. Lateral lobes — Approximately 0.8 cm. Width — Central lobe — Approximately 1.7 cm at the base; 0.9 at the apex. Lateral lobes — Approximately 0.8 cm. Apex — Central lobe — Emarginate. Lateral lobes — Obtuse. Base — Central lobe — Truncate. Lateral lobes — Cuneate. Margin — Central lobe — Entire; moderately undulated. Lateral lobes — Entire; not undulated. Texture and luster of upper surface — Central lobe — Glabrous, velvety, and slightly glossy towards the apex. Lateral lobes — Glabrous, velvety, and matte. Texture and luster of lower surface — Central lobe — Glabrous, velvety, and very slightly glossy. Lateral lobes — Glabrous, velvety, and matte. Color when opening, upper surface — Central lobe — Greyed-purple, nearest to a mixture of RHS N186A and N186B, and becoming purple towards the base, nearest to RHS N79B. Lateral lobes — Purple, nearest to RHS N77B, and becoming greyed-red at and near the apex, nearest to RHS 182C; radially striped purple, nearest to RHS 76D. Color when opening, lower surface — Central lobe — Purple, nearest to RHS N79B, and fading to a lighter shade of purple towards the base, nearest to RHS 79D; becoming greyed-purple at and near the apex, nearest to RHS N186B. Lateral lobes — Purple, nearest to RHS N77C, and radially striped green-white, nearest to RHS 157A. Color when fully opened, upper surface — Central lobe — Greyed-purple, nearest to RHS N186A, and becoming purple towards the base, nearest to RHS N79A. Lateral lobes — Purple, nearest to RHS N77C, and radially striped green-white, nearest to RHS 157B. Color when fully opened, lower surface — Central lobe — Purple, nearest to RHS N79B, and fading to a lighter shade of purple towards the base, nearest to RHS 79D; becoming greyed-purple at and near the apex, nearest to RHS N186B. Lateral lobes — Purple, nearest to RHS N77C, and radially striped green-white, nearest to RHS 157A. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities.*—Dimensions — 1.0 cm long and 0.8 cm wide, on average. Color — Greyed-purple, nearest to RHS N186A, and fading to purple towards the base, nearest to RHS N79A.

*Spurs.*—Quantity — Average of 1. Length — Approximately 0.8 cm. Diameter — Approximately 0.4 cm. Vertical height — Approximately 0.7 cm, at the base. Shape — Short triangular; flattened. Apex — Bluntly acute. Base — Broad cuneate. Pubescence, texture and luster — Glabrous, smooth, and matte. Color — Purple, nearest to RHS 77C, and radially striped green-white, nearest to RHS 157A.

*Sepals.*—Quantity — Average of 3 unfused sepals. Arrangement — One dorsal sepal and two lateral sepals. Length — Dorsal sepal — Approximately 4.8 cm. Lateral sepals — Approximately 4.9 cm. Width — Dorsal sepal — Approximately 5.3 cm. Lateral sepals — Approximately 4.6 cm. Shape — Dorsal sepal — Broad ovate. Lateral sepals — Broad ovate. Apex — Dorsal sepal — Obtuse. Lateral sepals — Obtuse. Base — Dorsal sepal — Cuneate. Lateral sepals — Cuneate. Margin — Dorsal sepal — Entire; lightly undulated. Lateral sepals — Entire; lightly undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — Purple, nearest to RHS N79B; becoming a lighter shade of purple at and near the base, nearest to RHS 76B; becoming purple-violet towards the apex, nearest to RHS N81A; sepal is dotted purple, nearest to RHS N79A. Lateral sepals — Nearest to in between purple and greyed-purple, RHS N79A and N186C; margined purple-violet, nearest to RHS N81A; base is purple, nearest to RHS 76B; sepal is lightly dotted purple towards the base, nearest to RHS N79B. Color when opening, lower surface — Dorsal sepal — Purple-violet, nearest to RHS N82A. Lateral sepals — Nearest to in between purple and purple-violet, RHS N79B and N81A; becoming violet towards the margins and apex, nearest to RHS 83B; becoming green-white towards the base, nearest to RHS 157A. Color when fully opened, upper surface — Dorsal sepal — Purple, nearest to in between RHS N78A and N79D; becoming a lighter towards the base, nearest to RHS 78D; base is purple, nearest to RHS 76B; becoming purple-violet towards the apex, nearest to RHS N81B; sepal is dotted purple, nearest to in between RHS N77A and N79A. Lateral sepals — Nearest to in between purple and greyed-purple, RHS N79A and N186B; margined purple-violet, nearest to RHS N81B; base is purple, nearest to RHS 76B; sepals are lightly dotted purple towards the base, nearest to in between RHS N79B and N79C. Color when fully opened, lower surface — Dorsal sepal — Purple-violet, nearest to RHS N82A, and fading to green-white towards the base, nearest to RHS 157A. Lateral sepals — Purple-violet, nearest to RHS N81A, and fading to green-white towards the base, nearest to RHS 157A. Fading, upper surface — Not fading. Fading, lower surface — Not fading. Venation color, fully opened, upper surface — Dorsal sepal — Purple, nearest to in between RHS N78A and N79D; becoming a lighter towards the base, nearest to RHS 78D; base is purple, nearest to RHS 76B; becoming purple-violet towards the apex, nearest to RHS N81B; sepals are finely dotted purple, nearest to in between RHS N77A and N79A. Lateral sepals — Nearest to in between purple and greyed-purple, RHS N79A and N186B; margined purple-violet, nearest to RHS N81B; base is purple, nearest to RHS 76B; sepals are lightly dotted purple towards the base, nearest to in between RHS N79B and N79C. Venation color, fully opened, lower surface — Dorsal sepal — Purple-violet, nearest to RHS N82A, and fading to green-white towards the base, nearest to RHS 157A. Lateral sepals — Purple-violet, nearest to RHS N81A, and fading to green-white towards the base, nearest to RHS 157A.

*Pedicels.*—Length — Approximately 4.9 cm. Diameter — Approximately 0.6 cm. Attitude — Approximately 95 degree angle to peduncle axis. Strength — Moderately strong. Texture — Glabrous, axially angled with 5 "ribs", axially twisted (due to resupination). Luster — Glossy. Color — Purple-violet, nearest to RHS N81A, and fading to purple towards the proximal end, nearest to RHS N79B.

*Bract.*—Quantity — One bract present at the base of each pedicel. Shape — Broad oblong; folded around the base of each pedicel. Dimensions — Average of 1.8 cm long and 1.6 cm wide. Apex — Broad obtuse. Base — Broad cuneate. Margins — Entire. Color, inner surface — Yellow-green, nearest to RHS N144C, and suffused with greyed-purple at the apex, nearest to RHS 187B. Color, outer surface — Yellow-green, nearest to RHS N144C, and suffused with greyed-purple at the apex, nearest to RHS 187B.

Reproductive organs:

*Column.*—Length — Approximately 0.7 cm. Diameter — Approximately 0.8 cm. Color — Yellow-white, nearest to RHS 158B; base is suffused with purple, nearest to RHS 77B.

*Ovary.*—Position — Inferior. Diameter — Approximately 0.2 cm. Color — Yellow-green, nearest to RHS 150D.

*Pollinia color.*—Yellow-orange, nearest to RHS 15A.

Seed and fruit: No fruit and seed production has been detected to date.

Comparison with the parent plants: Plants of the new cultivar 'SPCDW1801' differ from the *Vanda* seed parent, 'D25M' (not patented), by the characteristics described in Table 1.

TABLE 1

| Characteristic | 'SPCDW1801' | 'D25M' |
|---|---|---|
| Bloom habit. | More freely flowering. | Less freely flowering. |
| Inflorescence height. | Shorter than 'D25M'. | Longer than 'SPCDW1801'. |
| Quantity of flowers per inflorescence. | Fewer flowers than 'D25M'. | More flowers than 'SPCDW1801'. |

TABLE 1-continued

| Characteristic | 'SPCDW1801' | 'D25M' |
|---|---|---|
| Flower size. | Larger than 'D25M'. | Smaller than 'SPCDW1801'. |
| General coloration of the petals and sepals when fully opened. | Dark purple-violet. | Red-purple. |

Plants of the new cultivar 'SPCDW1801' differ from the *Vanda* pollen parent, *Vanda* '370MK' (not patented), by the characteristics described in Table 2.

TABLE 2

| Characteristic | 'SPCDW1801' | '370MK' |
|---|---|---|
| Growth habit. | More symmetrical growth. | Less symmetrical growth. |
| Bloom habit. | Less freely flowering. | More freely flowering. |
| Attitude of the inflorescence. | More upright. | Less upright. |
| Peduncle strength. | Stronger than | Weaker than 'SPCDW1801'. |
| Quantity of flowers per inflorescence. | More flowers than '370MK' | Fewer flowers than 'SPCDW1801'. |
| Flower size. | Smaller than '370MK'. | Larger than 'SPCDW1801'. |
| General coloration of the petals and sepals when fully opened. | Dark purple-violet. | Blue. |

Comparison with the most similar *Vanda* cultivar known to the inventor: Plants of the new cultivar 'SPCDW1801' are similar to the cultivar, *Vanda* 'SPCDW0802' (Community Plant Variety Rights grant number 28273). A comparison of 'SPCDW1801' with *Vanda* 'SPCDW0802' is described in Table 3.

TABLE 3

| Characteristic | 'SPCDW1801' | 'SPCDW0802' |
|---|---|---|
| Apex of the flower petals and sepals. | Obtuse. | Oblique. |
| Lateral sepal position. | More overlapping. | Less overlapping. |
| Margin undulation of the flower petals and sepals. | Less undulated. | More heavily undulated. |
| General coloration of the petals and sepals when fully opened, excluding the reticulation. | Dark purple-violet. | Violet-blue. |

That which is claimed is:

1. A new and distinct variety of *Vanda* plant named 'SPCDW1801', substantially as described and illustrated herein.

* * * * *